United States Patent
McKee (12) 
(10) Patent No.: US 10,605,807 B2
(45) Date of Patent: Mar. 31, 2020

(54) METHODS AND COMPOSITIONS FOR FLUORESCENCE DETECTION

(71) Applicant: Bio-Rad Laboratories, Inc., Hercules, CA (US)

(72) Inventor: Clayton T. McKee, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 208 days.

(21) Appl. No.: 15/441,024

(22) Filed: Feb. 23, 2017

(65) Prior Publication Data

US 2017/0242002 A1 Aug. 24, 2017

Related U.S. Application Data (60) Provisional application No. 62/299,436, filed on Feb. 24, 2016.

(51) Int. Cl.
| | | |
|---|---|---|
| *G01N 33/53* | (2006.01) | |
| *G01N 33/543* | (2006.01) | |
| *G01N 21/64* | (2006.01) | |
| *G01N 33/545* | (2006.01) | |
| *G01N 33/548* | (2006.01) | |

(52) U.S. Cl.
CPC ... *G01N 33/54393* (2013.01); *G01N 21/6428* (2013.01); *G01N 33/545* (2013.01); *G01N 33/548* (2013.01); *G01N 2021/6432* (2013.01)

(58) Field of Classification Search
CPC .......... G01N 33/548; G01N 33/5306
See application file for complete search history.

(56) References Cited

U.S. PATENT DOCUMENTS

| | | | |
|---|---|---|---|
| 2001/0046688 A1 | 11/2001 | Giri | |
| 2006/0172385 A1* | 8/2006 | Ernst | C07K 14/245 435/69.1 |
| 2006/0188929 A1 | 8/2006 | Morel et al. | |
| 2009/0155777 A1 | 6/2009 | Yang et al. | |
| 2014/0322727 A1 | 10/2014 | Isaksen et al. | |
| 2015/0031145 A1 | 1/2015 | McKee et al. | |
| 2015/0306223 A1 | 10/2015 | Conley et al. | |

FOREIGN PATENT DOCUMENTS

| | | |
|---|---|---|
| EP | 1167970 A1 | 1/2002 |
| WO | 2012/161288 A1 | 11/2012 |

OTHER PUBLICATIONS

International Search Report and Written Opinion from PCT/US17/19084; dated May 15, 2017; 11 pages.
Extended European Search Report for EP17757190.8 dated Sep. 19, 2019; 9 pages.
U.S. Dairy Export Council: "Nutritional composition of skim milk powder"; Jan. 1, 2005; retrieved from the Internet at https://www.dairyglobalnutrition.org/nutrition/milk-powder; 1 page.

* cited by examiner

*Primary Examiner* — Tracy Vivlemore
*Assistant Examiner* — Nam P Nguyen
(74) *Attorney, Agent, or Firm* — Kilpatrick Townsend and Stockton LLP (57) ABSTRACT

Methods and compositions for imaging and scanning Western or immunoblots are disclosed herewith.

12 Claims, 8 Drawing Sheets

METHODS AND COMPOSITIONS FOR FLUORESCENCE DETECTION

CROSS-REFERENCES TO RELATED APPLICATIONS

This application claims the benefit of U.S. Provisional Application No. 62/299,436, filed Feb. 24, 2016, which is incorporated in its entirety herein for all purposes.

BACKGROUND

Western or dot blotting is routinely used as an analytical technique to detect various proteins. Fluorescence detection is a method of choice in most Western and dot blot assays to visualize and quantify proteins. However, the nitrocellulose, polyvinylidene fluoride (PVDF), or other membranes common to the assays can scatter incident light, making protein quantification difficult. Thus, there is a need in the art to provide novel methods and compositions to solve this light scattering problem.

BRIEF SUMMARY

In general, provided herein are methods and compositions for the detecting and/or quantifying of fluorescent signals on a nitrocellulose, PVDF, or other suitable membrane used in Western blotting or another analytical technique. The inventors have discovered that an aqueous mixture of a sugar and a surfactant provides a solution which both decreases the background signal of standard capture membranes (e.g., PVDF, nitrocellulose) and increases the signal of fluorescent detection reagents. The solution, which can also include a buffer, can be used, for example, as a final membrane incubation solution of a Western blot detection workflow to improve detection of target proteins.

One provided composition includes 70% weight/volume (w/v) or more of a sugar, and a zwitterionic surfactant. The sugar and the zwitterionic surfactant are dissolved in water or an aqueous buffer. In some embodiments, the zwitterionic surfactant of the composition is an aminosulfobetaine. In some embodiments, the aminosulfobetaine is 3-(dimethyl(3-(4-octylbenzamido)propyl)ammonio)propane-1-sulfonate (ASB-C80). In some embodiments, the zwitterion surfactant concentration is within the range from about 0.01% to about 0.2% volume/volume (v/v). In some embodiments, the sugar of the composition is selected from the group consisting of sucrose, glucose, maltose, lactose, dextrose, cellobiose, and galactose. In some embodiments, the sugar concentration of the composition is within the range from about 70% to about 90% w/v. In some embodiments, the composition further includes a membrane submerged in the water or aqueous buffer, wherein the membrane is configured for use in an analyte detection assay. In some embodiments, the membrane of the composition includes nitrocellulose or PVDF. In some embodiments, the analyte detection assay is a Western blot.

Also provided is a method of imaging a membrane in an analyte detection assay, the method including submerging a membrane in a solution. The membrane is configured for use in an analyte detection assay. The solution includes a sugar and a zwitterionic surfactant, wherein the sugar and the zwitterionic surfactant are dissolved in water or an aqueous buffer. The method further includes imaging the membrane. In some embodiments, the membrane of the method includes nitrocellulose or PVDF. In some embodiments, the analyte detection assay is a Western blot. In some embodiments, the zwitterionic surfactant of the method is an aminosulfobetaine. In some embodiments, the aminosulfobetaine of the method is 3-(dimethyl(3-(4-octylbenzamido)propyl)ammonio)propane-1-sulfonate (ASB-C80). In some embodiments, the zwitterionic surfactant concentration of the method is within the range from about 0.01% to about 0.2% v/v. In some embodiments, the sugar of the method is selected from the group consisting of sucrose, glucose, maltose, lactose, dextrose, cellobiose, and galactose. In some embodiments, the sugar concentration of the method is within the range from about 70% to about 90% w/v.

Also provided is a kit for detecting an analyte, the kit including a sugar, a zwitterionic surfactant, and a buffer. In some embodiments, the zwitterionic surfactant of the kit is an aminosulfobetaine. In some embodiments, the aminosulfobetaine of the kit is 3-(dimethyl(3-(4-octylbenzamido)propyl)ammonio)propane-1-sulfonate (ASB-C80). In some embodiments, the sugar of the kit is selected from the group consisting of sucrose, glucose, maltose, lactose, dextrose, cellobiose, and galactose. In some embodiments, the kit further includes a binding agent.

DEFINITIONS

Unless defined otherwise, technical and scientific terms used herein have the same meaning as commonly understood by a person of ordinary skill in the art. See, e.g., Lackie, Dictionary of Cell and Molecular Biology, Elsevier (4th ed. 2007); and Sambrook et al., Molecular Cloning: A Laboratory Manual, Cold Spring Harbor Lab Press (Cold Spring Harbor, N.Y. 1989 and subsequent editions). The term "a" or "an" is intended to mean "one or more." The term "comprise," and variations thereof such as "comprises" and "comprising," when preceding the recitation of a step or an element, are intended to mean that the addition of further steps or elements is optional and not excluded. Methods, devices, and materials similar or equivalent to those described herein can be used in the practice of this invention. The following definitions are provided to facilitate understanding of certain terms used frequently and are not meant to limit the scope of the present disclosure. Abbreviations used herein have their conventional meaning within the chemical and biological arts.

As used herein, the term "sugar" refers to a monosaccharide, a disaccharide, an oligosaccharide, or a polysaccharide. Monosaccharides include, but are not limited to, glucose, ribose, fructose, mannose, xylose, arabinose, and galactose. Disaccharides include, but are not limited to, sucrose, lactose, cellobiose, and maltose. Polysaccharides include, but are not limited to, cellulose, hemicellulose and lignocellulose or starch. Other sugars are useful in the present invention.

As used herein, the term "surfactant" refers to a surface active agent that is used to lower the surface tension between liquids or a liquid and a solid. Surfactants can act as detergents, wetting agents, emulsifiers, foaming agents, or dispersants.

As used herein, the term "zwitterionic surfactant" refers to an amphiphilic surfactant molecule having no net charge that includes a hydrophobic group and one or more hydrophilic groups, as well as two moieties of opposite formal charges.

As used herein, the term "buffer" refers to any inorganic or organic acid or base that resists changes in pH and maintains the pH of a solution to which it is added around a desired point.

As used herein, the term "membrane" refers to a polymeric sheet of material that is used to expose analytes on its surface that can be detected by suitable chemistry. The analytes can be transferred to the membrane by electroblotting from an electrophoresed gel.

As used herein, the terms, "analyte", "antigen", and "target" refer to any molecule, compound, or complex of interest, whose presence, amount, expression level, activation state, and/or identity is determined. The determination can be through specific recognition by a binding agent. The molecule, compound, or complex of interest can be a macromolecule such as a polypeptide or protein, a polysaccharide, a toxin, a cell wall, a cell capsule, a viral capsule, a viral coat, a flagellum, a fimbria or pilus, a microorganism, a nucleic acid complexed to a protein or a polysaccharide, a lipid, a lipid complexed to a protein or a polysaccharide, a polynucleotide, a polypeptide, a carbohydrate, chemical moiety, or combinations thereof (e.g., phosphorylated or glycosylated polypeptides, etc.). One of skill will understand that the term does not indicate that the analyte is immunogenic in every context, but simply indicates that it can be targeted by a binding agent or an antibody.

As used herein, the term "binding agent" refers to a molecule that specifically binds to an antigen or analyte. Exemplary binding agents include, but are not limited to, an antibody, an antibody fragment, a non-antibody protein scaffold, an antibody mimetic, an aptamer, an affimer, a quenchbody, an antibody labeled with an enzyme, or an analyte-specific antibody pair.

As used herein, the term "binds" with respect to a binding agent and a target refers to a binding agent attaching to a majority of the targets in a pure population, assuming an appropriate molar ratio of binding agent to target. For example, a binding agent that binds a given target typically binds to at least ⅔ of the targets in a solution (e.g., 75%, 80%, 85%, 90%, 91%, 92%, 93%, 94%, 95%, 96%, 97%, 98%, 99%, or 100%). One of skill will recognize that some variability will arise depending on the affinity of the binding agent for the target as well as the method and/or threshold of determining binding.

As used herein, the terms "specifically binds" or "specific for" refer to the binding of a molecule (e.g., binding agent) that to a target with at least 2-fold greater affinity than to non-target compounds, e.g., at least 4-fold, 5-fold, 6-fold, 7-fold, 8-fold, 9-fold, 10-fold, 20-fold, 25-fold, 50-fold, or 100-fold greater affinity. When using one or more detectable analytes that are proteins, specific binding is determinative of the presence of the protein, in a heterogeneous population of proteins and other biologics. Thus, under designated immunoassay conditions, the specified antibodies bind to a particular protein sequence, thereby identifying its presence.

As used herein, the term "antibody" refers to a polypeptide of the immunoglobulin family or a polypeptide comprising fragments of an immunoglobulin that is capable of noncovalently, reversibly, and in a specific manner binding to an epitope of a corresponding antigen. The term includes, but is not limited to, polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies. The term encompasses conjugates, including but not limited to fusion proteins containing an immunoglobulin moiety (e.g., chimeric or bispecific antibodies or single chain Fv's (scFv's)), and fragments, such as Fab, F(ab')2, Fv, scFv, Fd, dAb and other compositions.

As used herein, the term "epitope" refers to the localized site on the antigen that is recognized and bound by the antibody. Protein epitopes can include a few amino acids or portions of a few amino acids, e.g., 5 or 6 or more, or 20 or more amino acids or portions of those amino acids. Epitopes can also include non-protein components, e.g., nucleic acid (e.g., RNA or DNA), carbohydrate, lipid, or a combination thereof. The epitope can be a three-dimensional moiety. Thus, for example, when the target is a protein target, the epitope can include consecutive amino acids, or amino acids from different parts of the protein that are brought into proximity by protein folding (e.g., a discontinuous epitope). The same is true for other types of target molecules, such as DNA and chromatin, which form three-dimensional structures.

As used herein, the terms "label" and "detectable label" refer to compositions detectable by spectroscopic, photochemical, biochemical, immunochemical, chemical, or other physical means. Useful labels include fluorescent dyes (fluorophores), fluorescent quenchers, luminescent agents, electron-dense reagents, enzymes (e.g., as commonly used in an ELISA), biotin, digoxigenin, $^{32}P$ and other isotopes, haptens, proteins, nucleic acids, or other substances which can be made detectable, e.g., by incorporating a label into or linking a label to an oligonucleotide, peptide, or antibody specifically reactive with a target molecule. The terms include combinations of single labeling agents, e.g., a combination of fluorophores that provides a unique detectable signature, e.g., at a particular wavelength or combination of wavelengths.

As used herein, the term "linked" with respect to a label and a binding agent (e.g., a labeled antibody as described herein) refers to a label that is bound, either covalently through a linker or a chemical bond, or noncovalently through ionic, van der Waals, electrostatic, or hydrogen bonds, to a binding agent such that the presence of an analyte can be detected by measuring the presence of the label linked to the binding agent.

As used herein, the terms "polypeptide", "peptide", and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

As used herein, the terms "Western blotting", "Western blot", or "protein immunoblot" refer to an analytical technique used to detect specific proteins in a sample of interest, biological or otherwise. The technique can use gel electrophoresis or other suitable procedures to separate proteins by size, shape, length, charge, or other characteristics. The proteins can then be transferred to a membrane and detected with binding agents that can be specific to one or more target proteins.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

DETAILED DESCRIPTION

I. General

Western blotting was first described in 1979 by Towbin et al. ((1979) *Proc. Natl. Acad. Sci USA* 76:4350), and has since been used for protein detection and quantitation using antibodies or other detection means. Early applications of this technique relied on antibody-enzyme conjugates that included horseradish peroxidase or alkaline phosphatase and were only semi-quantitative. Later protocols took advantage of developments such as fluorescent and chemiluminescent dye labels that provided more quantitative measurements of proteins. However, the inherent autofluorescence of the membranes associated with these techniques has remained an unresolved issue.

Herein are described novel approaches to reduce the autofluorescence of the membranes of Western blots and other analytical procedures, as well as to increase the fluorescence intensity of fluorophore labels used to detect and quantify target analytes. The present invention provides compositions and methods that include particular solutions of a sugar and a surfactant. The inventors have discovered that solutions having specific concentration ranges of sugar minimize the impact of autofluorescence and light scattering when imaging a membrane submerged within. The inventors have also discovered that the addition of a surfactant to the sugar solution serves to at least partially mitigate quenching of desired fluorescence emissions associated with detection of target analytes of interest.

II. Compositions

Several compositions are provided herein. The compositions can be used as imaging solutions for an analyte detection assay. The analyte detection assay can be a Western blot. It has been observed that the addition of a sugar to the composition can reduce autofluorescence or light scattering when imaging a membrane submerged within the composition.

The sugar of the composition can be any sugar that is highly water soluble. For example, sucrose, fructose, glucose, maltose, dextrose, or lactose can be used. Other monosaccharides, disaccharides and polysaccharides can also be used. For example, the sugar can be a monosaccharide such as xylose, fucose, tagatose, galactosamine, glucosamine, mannosamine, galactose, mannose, galacturonic acid, glucuronic acid, iduronic acid, mannuronic acid, N-acetyl galactosamine, N-acetyl glucosamine, N-acetyl mannosamine, N-acetyl muramic acid, 2-keto-3-deoxy-glycero-galacto-nononic acid, N-acetyl neuraminic acid, or N-neuraminic acid. The sugar can be a disaccharide such as lactulose, trehalose, cellobiose, isomaltose, isomaltulose, trehalulose, or chitobiose. The sugar can be a polysaccharide such as dextrin, glycogen, starch, cellulose, hemicellulose, polydextrose, inulin, beta-glucan, pectin, psyllium husk mucilage, beta-mannan, glucomannan, arabinoxylan, agra, alginate, carrageenan, chitin, chitosan, or various gums. The sugar can be a D-isomer, an L-isomer, or a mixture thereof. The sugar can be a methylate, acetate, phosphate, or sulfate derivative of another sugar. The composition can include a mixture of two or more sugars in any ratio. Other highly water soluble polymers, e.g., polyethylene glycol, polylactic acid, etc., can also be useful in rendering the membrane translucent to transparent.

The amount of sugar required to reduce autofluorescence and light scatter can depend on the thickness of the membrane submerged in the solution, and the excitation and emission wavelengths of the fluorophores of interest. In general, about 70% to 100% or more weight/volume of sugar in the solution has been found to make submerged membranes appear transparent to almost translucent. The amount of sugar in the composition can be within the range from 50% to 80%, from 60% to 90%, from 70% to 100%, from 80% to 110%, or from 90% to 120% weight/volume. The amount of sugar in the composition can be within the range from 70% to 82%, from 72% to 84%, from 74% to 86%, from 76% to 88%, or from 78% to 90% weight/volume. In some embodiments, the amount of sugar in the composition is within the range from 70% to 90% weight/volume. In some embodiments, the sugar concentration is within the range from 75% to 90% weight/volume. In some embodiments, the sugar concentration is about 70%, about 85%, or about 90% weight/volume.

The addition of sugar to a water or buffer solution can make a membrane submerged within the solution appear transparent to translucent. However, this addition of sugars can also lead to quenching of the fluorescent signal. To reduce quenching, a surfactant can also be added to the composition. The surfactant can be anionic, cationic, nonionic, or amphoteric. In some embodiments, the surfactant is a zwitterionic surfactant. The zwitterionic surfactant can be, for example, a sultaine, a betaine, a phospholipid, or a sphingolipid. The zwitterionic surfactant can be a sulfobetaine (SB), amidosulfobetaine (ASB) or octylbenzyl amido sufobetaine. The zwitterionic surfactant can be, for example, 3-((3-cholamidopropyl)dimethylammonio)-1-propanesulfonate (CHAPS), cocamidopropyl hydroxysultaine, cocamidopropyl betaine, phosphatidylserine, phosphatidylethanolamine, phosphotidylcholine, or sphingomyelin. The zwitterionic surfactant can be an aminosulfobetaine or aromatic aminosulfobetaine. In some embodiments, the zwitterionic surfactant is 3-(dimethyl(3-(4-octylbenzamido)propyl)ammonio)propane-1-sulfonate (ASB-C80). In one aspect, the surfactant is selected from SB 3-10, SB 3-12, SB 3-14, ASB-14, ASB-16, or ASB-C80. The composition can include a mixture of two or more surfactants in any ratio.

The amount of surfactant required to reduce quenching of fluorescence by the sugar can depend on the type and concentration of sugar in the solution, and the excitation and emission wavelengths of the fluorophores of interest. In general, about 0.01% to 0.2% or more volume/volume of surfactant in the solution has been found to reduce fluorescence quenching. The amount of surfactant in the composition can be within the range from 0.001% to 0.01%, from 0.002% to 0.2%, from 0.005% to 0.4%, from 0.01% to 0.9%, or from 0.02% to 2% volume/volume. The amount of surfactant in the composition can be within the range from 0.01% to 0.06%, from 0.015% to 0.08%, from 0.02% to 0.1%, from 0.025% to 0.15%, or from 0.035% to 0.2% volume/volume. In some embodiments, the concentration of surfactant is about 0.05%, about 0.1%, or about 0.2% volume/volume.

The sugar and surfactant can be dissolved in water or any aqueous buffer suitable for use with an analyte detection assay. The buffer can include, for example, 2-amino-2-(hydroxymethyl)propane-1,3-diol (Tris), Tris-HCl, Tris-buffered saline (TBS), glycine, 2-(4-(2-hydroxyethyl)piperazin-1-yl)ethanesulfonic acid (HEPES), phosphate-buffered saline (PBS), or combinations thereof in any ratio. The analyte detection assay can be a Western blot. The composition can further include a membrane configured for use in the analyte detection assay, wherein the membrane is submerged in the water or aqueous buffer. The membrane can include, for example, nitrocellulose, polyvinylidene difluoride (PVDF), nylon, or combinations of two or more thereof in any ratio.

III. Methods

Also provided are several methods for imaging a membrane in an analyte detection assay. The methods can include submerging a membrane in a solution. The membrane can be configured for use in an analyte detection assay, as described above. In some embodiments, the analyte detection assay is a Western blot and the membrane includes nitrocellulose or PVDF. The solution can have any of the compositions described above. In some embodiments, the solution includes a sugar that is sucrose, glucose, maltose, lactose, dextrose, cellobiose, or galactose. In some embodiments, the concentration of the sugar in the solution is in the range from 70% to 90% weight/volume. In some embodiments, the solution includes a zwitterionic surfactant. The zwitterionic surfactant can be an aminosulfobetaine, such as ASB-C80. In some embodiments, the concentration of the surfactant in the solution is in the range from 0.01% to 0.2% volume/volume.

The methods can further include imaging the membrane. The imaging can be used to detect one or more analytes in any type of sample. In some embodiments, the sample is a biological sample. In some embodiments, the sample is a chemical or physical sample, e.g., water or a chemical solution or air or a rock. Biological samples can be obtained from any biological organism, e.g., an animal, plant, fungus, bacteria, viruses or prions, or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, transformed cells, stem cells, stool, or urine.

In some embodiments, the one or more analytes to be detected include peptides, proteins (e.g., antibodies, enzymes, growth regulators, clotting factors, or phosphoproteins), immunogens, polysaccharides, toxins, cell walls, cell capsules, viral capsules, viral coats, flagella, fimbriae or pili, microorganisms, nucleic acids complexed to protein or polysaccharide, or lipids complexed to protein or polysaccharide. In some embodiments, two, three, four, five, or more different analytes are detected. In some embodiments, wherein two or more different analytes are to be detected, the two or more different analytes are the same type of analytes (e.g., two or more proteins present in a complex). In some embodiments, wherein two or more different analytes are to be detected, the two or more different analytes are different types of analytes. The presently described methods and compositions can be useful as standalone single analyte assays wherein a single analyte is detected across different samples. Alternately, the methods and compositions are useful in detecting multiple analytes across many different samples separated on a transfer membrane.

The analytes can be detected with the use of a binding agent. A binding agent suitable for use according to the methods described herein is any molecule that specifically binds to an analyte (e.g., antigen) of interest. In some embodiments, the binding agent is an antibody or a portion thereof. In some embodiments, the binding agent as described herein is linked to a detectable label. The label can be linked directly to the binding agent (e.g., by a covalent bond) or the attachment can be indirect (e.g., using a chelator or linker molecule). The terms "label" and "detectable label" are used interchangeably herein and are described in detail below.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, and combinations thereof. In some embodiments, the label can include an optical agent such as a fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005).) Fluorescent agents can include a variety of organic and/or inorganic small molecules or a variety of fluorescent proteins and derivatives thereof. Literature sources for fluorophores include Cardullo et al. (1988) *Proc. Natl. Acad. Sci. USA* 85:8790-8794 (1988); Dexter (1953) *J. of Chemical Physics* 21:836-850; Hochstrasser et al. (1992) *Biophysical Chemistry* 45:133-141; Selvin (1995) *Methods in Enzymology* 246:300-334; Steinberg (1971) *Ann. Rev. Biochem.* 40:83-114; Stryer (1978) *Ann. Rev. Biochem.* 47:819-846; Wang et al. (1990) *Tetrahedron Letters* 31:6493-6496; and Wang et al. (1995) *Anal. Chem.* 67:1197-1203. Fluorescent dyes and fluorescent label reagents include those which are commercially available, e.g., from Invitrogen/Molecular Probes (Eugene, Oreg.) and Pierce Biotechnology, Inc. (Rockford, Ill.).

The following are non-limiting examples of fluorophores that can be used as labels: 4-acetamido-4'-isothiocyanatostilbene-2,2'disulfonic acid, acridine, acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate, N-(4-anilino-1-naphthyl)maleimide, anthranilamide, BODIPY, Brilliant Yellow, coumarin, 7-amino-4-methylcoumarin (AMC, Coumarin 120), 7-amino-4-trifluoromethylcoumarin (Coumaran 151), cyanine dyes, cyanosine, 4',6-diaminidino-2-phenylindole (DAPI), 5',5"-dibromopyrogallol-sulfonaphthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin, eosin isothiocyanate, erythrosin B, erythrosin isothiocyanate, ethidium, 5-carboxyfluorescein (FAM), 5-(4,6-dichlorotriazin-2-yl) aminofluorescein (DTAF), 2',7'-dimethoxy-4'5'-dichloro-6-carboxyfluorescein (JOE), fluorescein, fluorescein isothiocyanate, fluorescamine, IR144, IR1446, Malachite Green isothiocyanate, 4-methylumbelliferone, ortho cresolphthalein, nitrotyrosine, pararosaniline, Phenol Red, phycoerythrin (including but not limited to B and R types), o-phthaldialdehyde, pyrene, pyrene butyrate, succinimidyl 1-pyrene butyrate, quantum dots, Reactive Red 4 (CIBACRON™ Brilliant Red 3B-A), 6-carboxy-X-rhodamine (ROX), 6-carboxyrhodamine (R6G), lissamine rhodamine B sulfonyl chloride rhodamine, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, lanthanide chelate derivatives. In some embodiments, the optical agent is an intercalating dye. Intercalating dyes include, but are not limited to, SYBR Green and Pico Green (from Molecular Probes, Inc., Eugene, Oreg.), ethidium bromide, propidium iodide, chromomycin, acridine orange, Hoechst 33258, TOTO-I, YOYO-1, and DAPI (4',6-diamidino-2-phenyl indole hydrochloride).

A prominent group of fluorophores for immunoassays includes fluorescein, fluorescein isothiocyanate, phycoerythrin, rhodamine B, and Texas Red (sulfonyl chloride derivative of sulforhodamine 101). Any of the fluorophores in the list preceding this paragraph can be used in the presently described assays, either to label the microparticle, or to label a binding agent (e.g., an antibody or streptavidin). Fluorochromes can be attached by conventional covalent bonding, using appropriate functional groups on the fluorophores and on the microparticle or binding agent. The recognition of such groups and the reactions to form the linkages will be readily apparent to those skilled in the art.

In some embodiments, a fluorescent agent is a polymer dot or a quantum dot. The particular quantum dot (QD) employed is not critical to the present invention. Quantum dots are known in the art and are described, for example, by Han et al., "Quantum-dot-tagged Microbeads for Multiplexed Optical Coding of Biomolecules", *Nat Biotechnol.* (July 2001) vol. 19, pp. 631-635. One of skill in the art will appreciate the various quantum dots that can serve as fluorescent labels and that can be employed in embodiments of the invention and which are available from various commercial vendors. Exemplary quantum dots (QDs) include, but are not limited to, the following: cadmium selenide (CdSe) quantum dot nanoparticles (e.g., CdSe Quantum Dot Cores, 480-640 nm emission spectra, Sigma-Aldrich®); cadmium sulfide (CdS) quantum dot nanoparticles (e.g., CdS Quantum Dot Cores, 380-480 nm emission spectra, Sigma-Aldrich®); zinc sulfide-capped cadmium selenide (ZnS-capped CdSe) nanocrystals (e.g., CdSe/ZnS LUMIDOTS™ and CdSe/ZnS NANODOTS™, 480-640 nm emission spectra, Sigma-Aldrich®); and cadmium-free quantum dots (e.g., CFQD™, 400-650 nm emission spectra, Sigma-Aldrich®).

Techniques for attaching detectable labels to binding agents are known. For example, a review of common protein labeling techniques can be found in Biochemical Techniques: Theory and Practice, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996). The techniques are also available as parts of commercially available kits (e.g., THUNDER-LINK® and LIGHTNING-LINK® from Innova Biosciences Ltd., Cambridge, United Kingdom). Many suitably labeled binding agents are commercially available and can be used with or without further modifications. Other labels that can be used in place of the fluorophores are radioactive labels and enzyme labels. These are likewise known in the art.

IV. Kits

Also provided are several kits for detecting one or more analytes. The analytes can be any of the analytes described above. In some embodiments, the analytes are proteins. The kit includes a sugar and a surfactant. The sugar can include any one or more of the sugars described above. The surfactant can include any one or more of the surfactants described above. In some embodiments, the sugar is selected from the group consisting of sucrose, glucose, maltose, lactose, dextrose, cellobiose, and galactose; and the surfactant is an aminosulfobetaine. The kit can further include a buffer. The buffer can include any one or more of the buffer compounds described above. In some embodiments, the sugar, surfactant, and/or buffer are provided as dry ingredients to be combined by an enduser into an aqueous solution.

The kit can further include a membrane. The membrane can be any of the membranes described above. In some embodiments, the membrane is configured for use in an analyte detection assay. In some embodiments, the membrane is configured for use in a Western blot assay. In some embodiments, the membrane includes nitrocellulose or PVDF.

The kit can further include a binding agent. The binding agent can include any one or more of the binding agents described above. The kit can include, for example, one or more antibodies labeled with biotin, and/or an analyte-specific antibody pair, (strept)avidin, labeled biotin, e.g., phycoerythrin labeled biotin, beads, and control reagents, as described herein. In some embodiments, the kit further includes instructions for carrying out the methods described herein.

V. Examples

Example 1. Effect of Sugar Solution on Submerged Membrane Transparency

Both PVDF and nitrocellulose membranes scatter a large amount of light in air and water due to the porous nature of the solids and the large reflective index difference between the membrane (>1.45) and air (1.00) or water (about 1.33). If the refractive index between the solid and environment is matched, light no longer has a surface to scatter from and the membrane can appear almost transparent. This can be created by adding and further controlling the amount of sugar in a solution in which the membrane is submerged.

Figure 1:
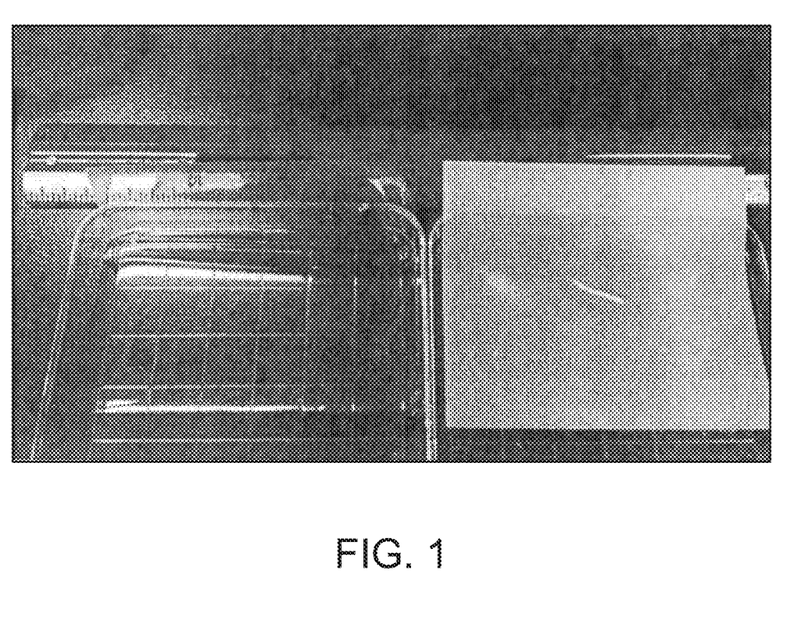
FIG. 1 is a photograph of polyvinylidene difluoride (PVDF) membranes submerged in an 85% w/v sugar solution or water.

Two similar PVDF membranes were immersed in an 85% sugar solution and water (FIG. 1). As can be seen from the figure, the left PVDF membrane immersed in the sugar solution becomes almost transparent. Such apparently transparent membranes have significantly reduced background signals when imaged with, for example, a ChemiDoc MP Imaging System (Bio-Rad).

Example 2. Effect of Surfactant on Fluorescence Quenching by Sugar

Figure 2:
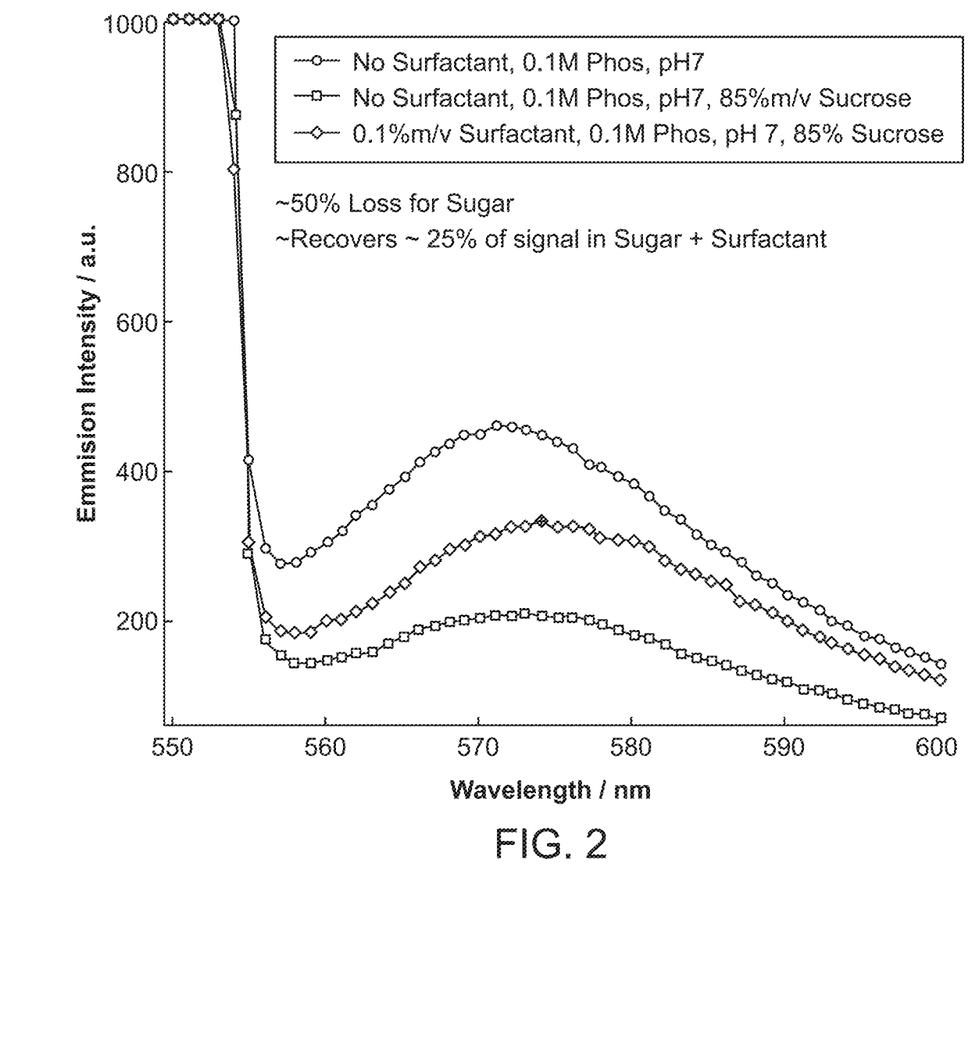
FIG. 2 is a graph showing the effects of a sugar and a surfactant on Western blot emission quenching.
Figure 3:
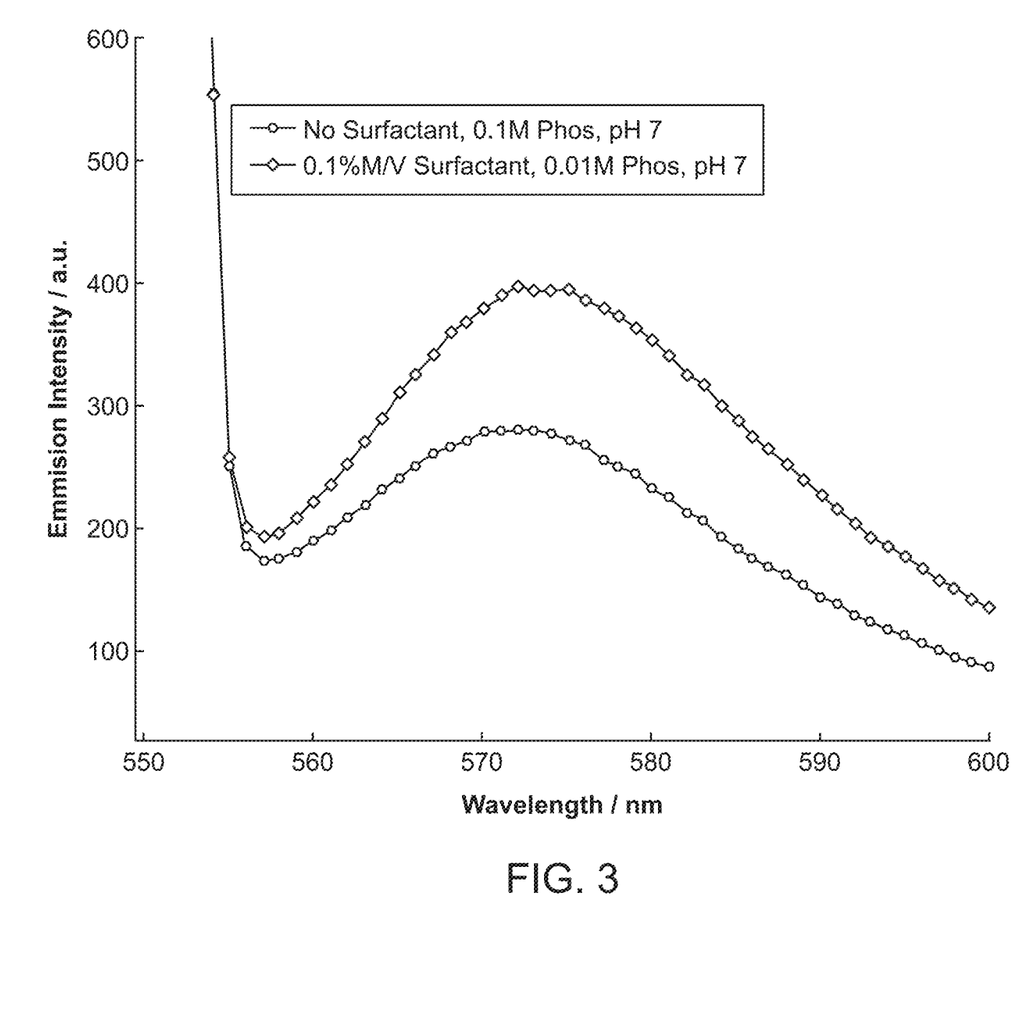
FIG. 3 is a graph showing the effects of a surfactant on Western blot emission intensities.

Sugars are polar molecules, and polar solvents typically quench fluorophores. FIG. 2 shows the emission spectrum of fluorophores in an aqueous sugar water. From the data in the graph, the emission intensity in neutral phosphate buffer is lowered by approximately 50% upon addition of 85% weight/volume sucrose. However, further addition of a surfactant (0.1% ASB-C80) to the sugar buffer solution reduces this sugar-induced quenching, such that approximately half of the lost intensity is recovered. Furthermore, the data of FIG. 3 shows that the addition of a surfactant (0.1% ASB-C80) to a phosphate or other standard buffer also increases the fluorescent signal from within the buffer.

Figure 4:
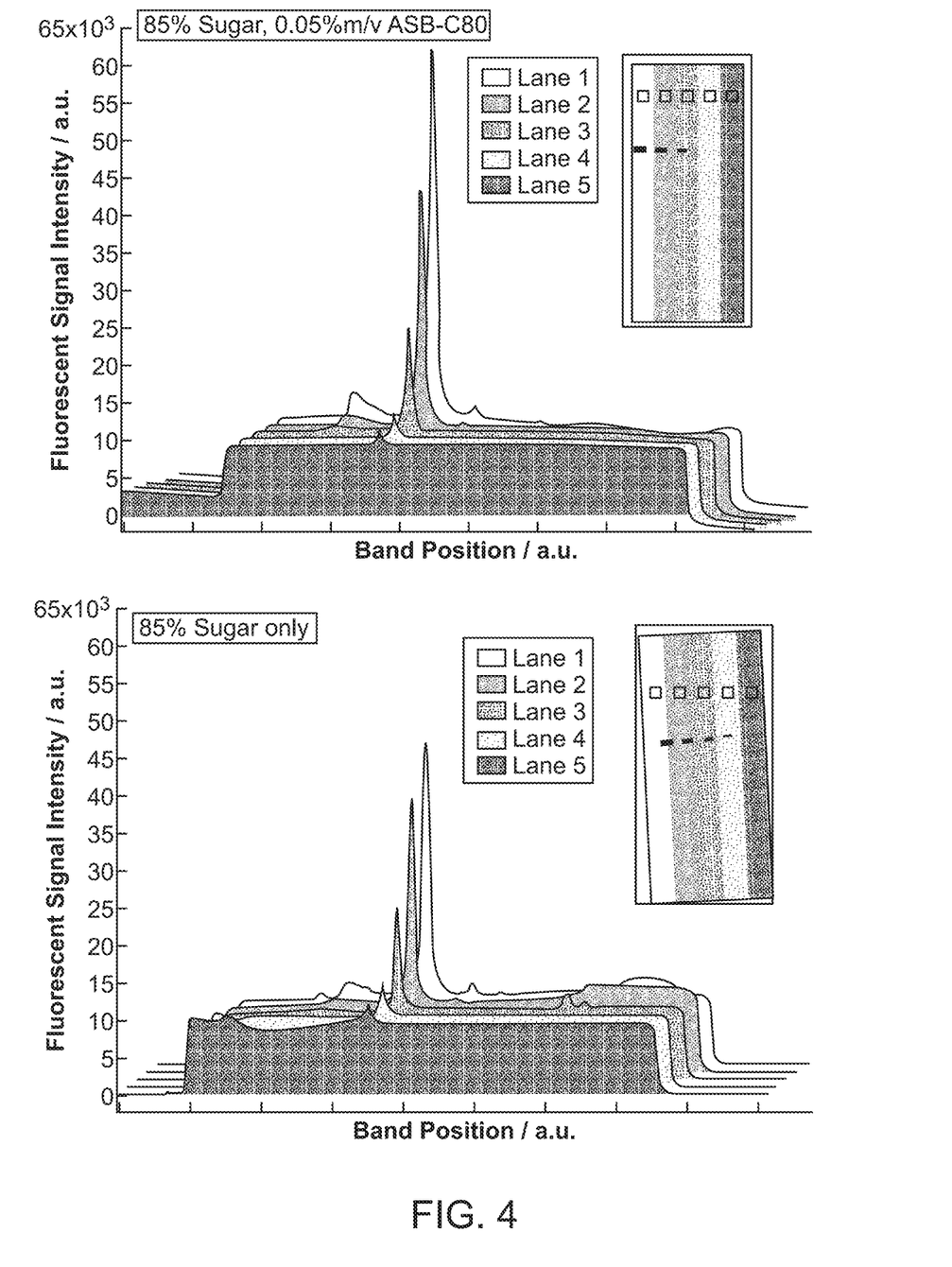
FIG. 4 presents graphs showing the effects of a sugar and a surfactant on Western blot emission intensities at different protein concentrations.

Example 3. Fluorescence Intensities of Blotted Proteins Imaged with Sugar and Surfactant Solutions FIG. 4 shows the signal intensities of detected proteins on a membrane soaked in sugar water compared to the intensities of detected proteins on a membrane soaked in sugar water plus surfactant. The two membranes were imaged simultaneously with identical exposure. The results shown indicate that the membrane soaked in sugar plus surfactant produces greater signal intensities, consistent with the fluorescent emission results of FIGS. 2 and 3.

Example 4. Imaging of Cell Lysate using Solution of Sugar and Surfactant

Figure 5:
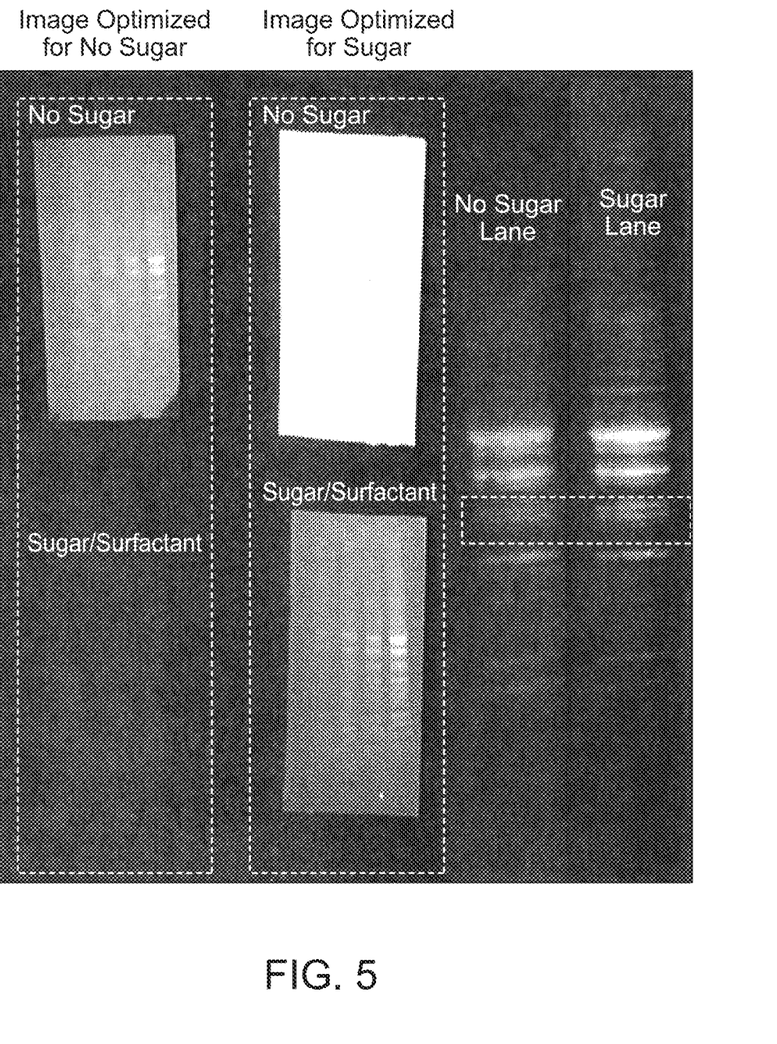
FIG. 5 presents photographs of membranes showing increased analyte resolution upon being submerged in a sugar/surfactant solution.
Figure 6:
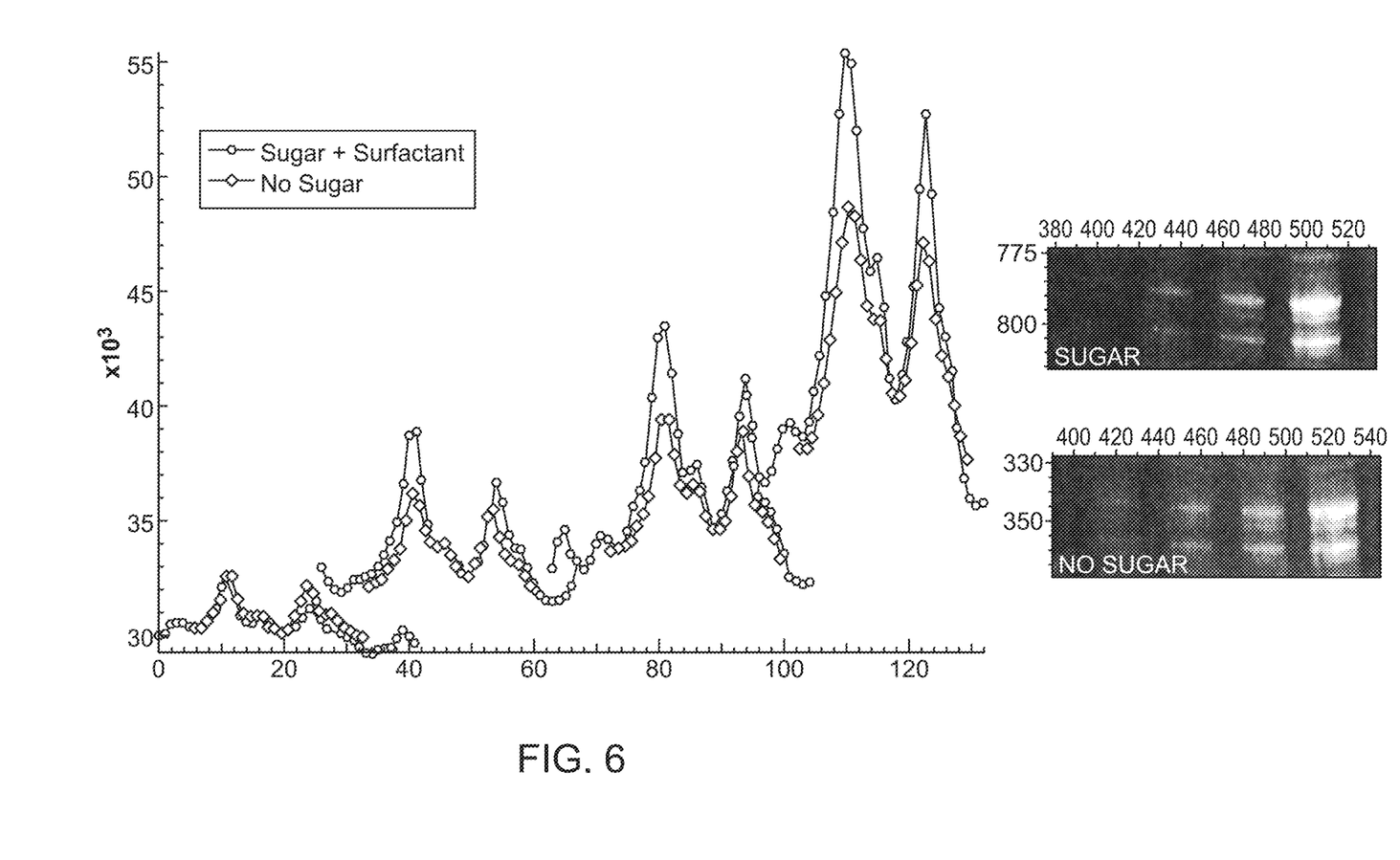
FIG. 6 presents photographs and a graph showing increased analyte resolution and emission intensities upon being submerged in a sugar/surfactant solution.

A separated cell lysate sample was blotted onto a PVDF membrane that was then imaged in the presence and ASBence of an aqueous buffer that included sugar and surfactant. From the images presented in FIG. 5 showing stain-free emission from the sample, it can be seen that the resolution of protein bands within the sample is enhanced when imaged using the sugar/surfactant buffer. From the graph in FIG. 6, a decrease in light scattering and an increase in emission intensity appears to coincide with the enhanced resolution for the case of imaging in the presence of sugar and surfactant.

Example 5. Effect of Surfactant Type and Concentration

Figure 7:
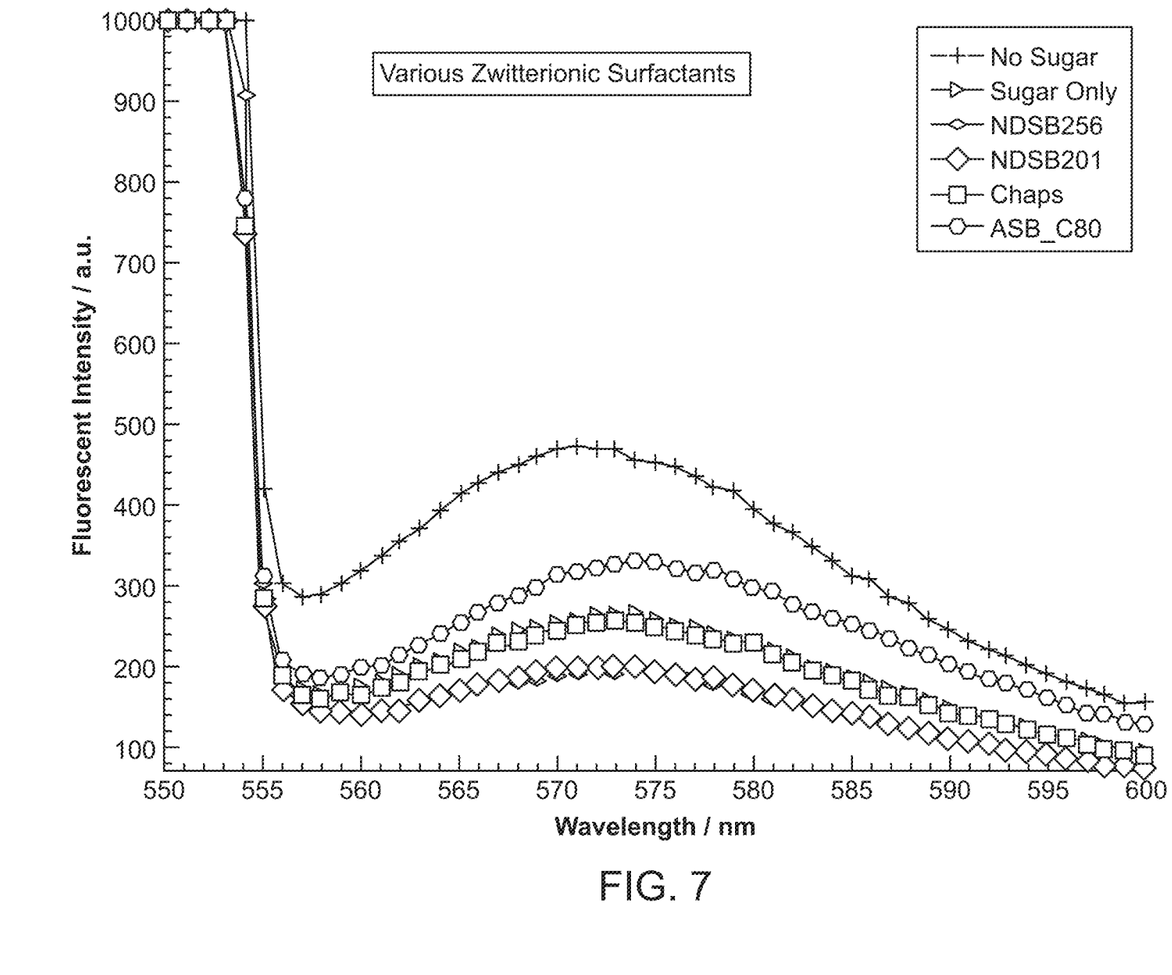
FIG. 7 is a graph showing the effects of different surfactants on Western blot emission quenching.
Figure 8:
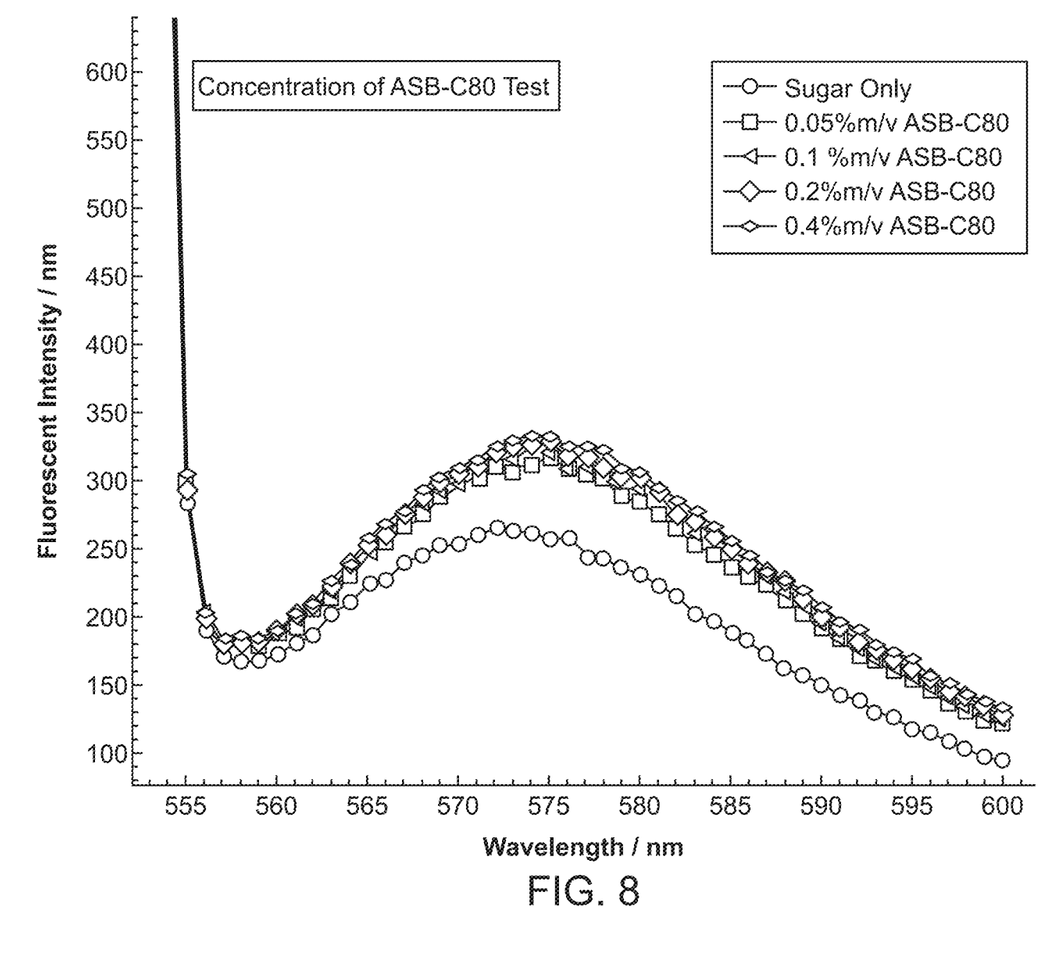
FIG. 8 is a graph showing the effects of surfactant concentration on Western blot emission quenching.

Four different zwitterionic surfactants were tested for their efficiency in reducing the quenching of fluorescence by sugar solutions. From the graph presented in FIG. 7, of these surfactants, the aromatic aminosulfobetaine ASB-C80 exhibited the best ability to alleviate quenching and produce images with the greatest fluorescence intensity. Further experiments were carried out to determine the concentration effects of ASB-C80 in reducing the fluorescent quenching. As shown in FIG. 8, all tested concentrations exhibited adequate reductions in quenching.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A composition comprising a membrane immersed in a solution, wherein the solution comprises:
   70% w/v or more of a sugar; and
   a zwitterionic surfactant, wherein the sugar and the zwitterionic surfactant are dissolved in water or an aqueous buffer; and
   the membrane is configured for use in an analyte detection assay.

2. The composition of claim 1, wherein the membrane comprises nitrocellulose or polyvinylidene difluoride (PVDF).

3. The composition of claim 1, wherein the zwitterionic surfactant is an aminosulfobetaine.

4. The composition of claim 3, wherein the aminosulfobetaine is 3-(dimethyl(3-(4-octylbenzamido)propyl)ammonio)propane-1-sulfonate (ASB-C80).

5. The composition of claim 1, wherein the sugar is selected from the group consisting of sucrose, glucose, maltose, lactose, dextrose, cellobiose, and galactose.

6. The composition of claim 1, wherein the sugar concentration is within the range from about 70% to about 90% w/v.

7. The composition of claim 1, wherein the zwitterionic surfactant concentration is within the range from about 0.01% to about 0.2% v/v.

8. A kit for detecting an analyte, the kit comprising:
   a solution comprising:
      at least 70% w/v or more of a sugar;
      a zwitterionic surfactant; and
      a buffer; and
   a membrane configured for use in an analyte detection assay.

9. The kit of claim 8, wherein the zwitterionic surfactant is an aminosulfobetaine.

10. The kit of claim 9, wherein the aminosulfobetaine is 3-(dimethyl(3-(4-octylbenzamido)propyl)ammonio)propane-1-sulfonate (ASB-C80).

11. The kit of claim 8, wherein the sugar is selected from the group consisting of sucrose, glucose, maltose, lactose, dextrose, cellobiose, and galactose.

12. The kit of claim 8, further comprising:
   a binding agent.

* * * * *